United States Patent
Liu

(10) Patent No.: US 11,871,989 B2
(45) Date of Patent: Jan. 16, 2024

(54) LASER FIBER PROBE WITH SUCTION

(71) Applicant: Yishuai Xiong, Denver, CO (US)

(72) Inventor: Huanjie Liu, Shenzhen (CN)

( * ) Notice: Subject to any disclaimer, the term of this patent is extended or adjusted under 35 U.S.C. 154(b) by 256 days.

(21) Appl. No.: 15/929,694

(22) Filed: May 16, 2020

(65) Prior Publication Data

US 2020/0397507 A1    Dec. 24, 2020

(30) Foreign Application Priority Data

Jun. 23, 2019   (CN) .......................... 201910535672.5

(51) Int. Cl.
  *A61B 18/26*   (2006.01)
  *A61M 25/00*   (2006.01)
  *A61M 1/00*   (2006.01)

(52) U.S. Cl.
  CPC .............. *A61B 18/26* (2013.01); *A61M 1/84* (2021.05); *A61M 25/0026* (2013.01); *A61B 2218/002* (2013.01); *A61B 2218/007* (2013.01); *A61M 1/77* (2021.05)

(58) Field of Classification Search
  CPC .............. A61B 18/26; A61B 2218/002; A61B 2218/007; A61B 2018/00511; A61B 2018/00982; A61B 2018/00517; A61M 1/0062; A61M 25/0026
  See application file for complete search history.

(56) References Cited

U.S. PATENT DOCUMENTS

| | | | |
|---|---|---|---|
| 2015/0196361 A1* | 7/2015 | Preiss | A61B 17/3421 606/15 |
| 2021/0121188 A1* | 4/2021 | Yurek | A61M 25/0147 |

* cited by examiner

*Primary Examiner* — Jonathan T Kuo

(57) ABSTRACT

A laser fiber probe comprises two parts, a suction sheath and a fiber conduit, which are combined together. The suction sheath has an opening in the distal end of the suction sheath and the opening is either completely in the side of the suction sheath, or in combination of part the terminal and the side. The fiber conduit has a fiber position regulator functioning to move forward or backward of the fiber tip to approach the suction opening. The relative position of the suction sheath and the fiber conduit of the fiber probe or is fixed, or can be changed through turning movement. The laser fiber probe further comprises a suction switcher to turn on or off the suction channel. The fiber probe has applications in calculus and tissue fragmentation and simultaneously evacuates them away out of the patient.

7 Claims, 4 Drawing Sheets

LASER FIBER PROBE WITH SUCTION

CROSS-REFERENCE TO RELATED APPLICATIONS

This patent was filed in China on Jun. 23, 2019 with the National Intellectual Property Administration, PRC. The application number is 201910535672.5.

STATEMENT REGARDING FEDERALLY SPONSORED RESEARCH OR DEVELOPMENT

N/A—Not Applicable

REFERENCE TO SEQUENCE LISTING, A TABLE, OR A COMPUTER PROGRAM LISTING COMPACT DISC APPENDIX

N/A—Not Applicable

BACKGROUND OF THE INVENTION

Urinary calculus is quite common and has high morbidity, and it can recur after surgery. Therefore, minimally invasive therapies are always pursued. The common minimally invasive surgeries are to fragment and then remove the concretions from the body of patient. To evacuate any debris of the stones as possible as doctor can is always the target. To evacuate the debris of the stone through vacuum is an efficient way.

Very successful lithotripter is ultrasonic equipment with vacuum suction and FIG. 1 illustrates the kidney stone are cured with ultrasonic lithotripter through PCLN. The ultrasonic probe 200 functions the fragmentation of the stone while evacuates the debris 03 and water 02 through the conduit 210 of which the other end 220 is connected to a vacuum source. This kind lithotripsy is recognized for its operation efficiency.

Lasers (disclosed by U.S. Pat. Nos. 5,387,211 and 5,963,575), especially the pulse infrared lasers, are another type of energy source, performing a very important role in minimally invasive surgeries. Different from ultrasonic, laser-induced fragmentation of concretions is always effective regardless of the types of stone. Distinguished from other energy sources, the laser energy can be delivered through flexible optical fibers, which facilitate its pass through the human organ natural path.

However, for laser lithotripsy, to fragment the stone 01 (FIG. 2) while evacuating the debris 03 as efficiently as ultrasonic is very challenging. Laser energy can fragment calculus but can also destroy the endoscope and the fiber tip itself. Therefore, the fiber tip 31 is handled to keep away from the sensitive camera of the endoscope, which is to protrude from the end terminations of the endoscope. By this means, it can not only overcome the risk of destroying the endoscope (especially the camera and illumination light), but also maintain good vision over the fiber tip which is always needed during laser procedures as shown in FIG. 2. However, as a result of this, the suction of the calculus 01 to the window of the suction is hindered by the protruding of the fiber tip.

As an alternative way, the irrigation water instead of the calculus and calculi pieces is sucked through the connection to a vacuum source, the fragmented stones are forced away by the flowing water. As disclosed in patent application with Chinese patent No. 201710402743.5, a piece of cannula is arranged as the hollow sheath around the inner conduit of an endoscope, forming a suction channel which the irrigated water and stone debris are evacuated through as shown in FIG. 2. The optical fiber probe reaches the calculus through the device channel of the endoscope. Another device disclosed in Chinese patent CN201692051, a cannula is invented to suck water together with stone pieces in a separated channel which works on the principle of the sucked water to force surgery debris. These devices do have improvements on evacuation of debris, but the doctors need additional efforts and attention to do so. Additionally the stones are difficult to be targeted due to its movement induced by laser pulse energy because they are not fixed by the suction. As a result, some laser energy from infrared laser pulse is consumed to warm water, and some laser energy forming shack wave is wasted because the surgery target is missed.

BRIEF SUMMARY OF THE INVENTION

A laser fiber probe comprising a suction sheath which has a window is in the distal end of the suction sheath and is used to suck the surgery targets and surgery debris, herein the proximal end of the suction sheath is adapted to connect to a suction source or an irrigation pump, a fiber conduit having a fiber position regulator functions at least to move forward or backward of the fiber laser window to approach thereof the suction window, the suction sheath and the fiber conduit being combined as a whole is disclosed.

In one embodiment of the invention, the suction window is opened completely on the side of the distal end of the suction sheath; In other embodiment, the suction window is opened completely in the end termination of the distal end of the suction sheath, In some embodiments, the suction window is opened in part of the distal end face and part of the side of sheath. For all embodiments mentioned above, the fiber conduit is bond to the outside of the suction sheath which has its axis paralleling to the axis of the suction sheath, the extending of the fiber axis is across the center line of the suction window.

In some embodiments, the fiber conduit can be arranged inside of the suction sheath.

In the embodiments the mutual position of the suction sheath and a fiber conduit is fixed, while in the other embodiment, the mutual position of the suction sheath and a fiber conduit can be changed through turning movement.

In the embodiments of the invention, the suction channel can include a switcher which can completely or partially turn on and turn off the suction channel. Another important role of the suction switcher can reposition the surgery targets against the suction window as well as the fiber laser window. In the laser fiber probe of the suction sheath with the suction window and the fiber conduit with fiber laser window, the suction window catches the surgery targets, where the fiber conduit positions the fiber laser window to contact and target the surgery targets. The said surgery targets are made into surgery debris under the action of laser energy emitted from the fiber laser window, coincidentally the debris is sucked through the said suction window and suction channel all the way out of patient's body.

The proximal end of the suction channel is adapted to connect to a vacuum source or an irrigation pump which can apply the suction in the suction window. Under the forces of the vacuum source or irrigation pump, the surgery targets are sucked to the position of the suction window and the fiber laser window. The calculus is fragmented and the tissues are cut into pieces, coincidentally those debris are evacuated away outside of the patient through the suction window and channel.

The disclosed fiber laser probe has very good control over the surgery targets, the debris, the interaction between the laser energy and the surgery targets, ultimately to reduce the surgery time, improve the surgery efficiency.

DETAILED DESCRIPTION OF THE INVENTION

Figure 1:
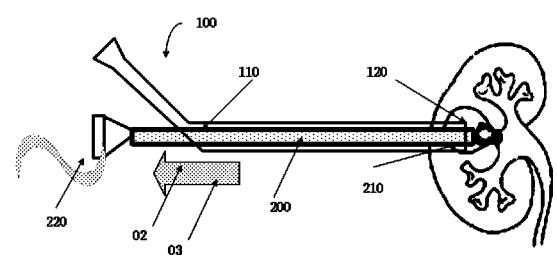
FIG. 1 illustrates the ultrasonic lithotripter for renal calculus under PCNL.
Figure 2:
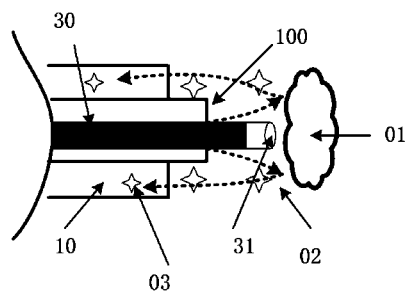
FIG. 2 illustrates the protruding fiber tip during the laser lithotripsy procedures.

A sheath with the diameter dimension are selected according to the inner diameter of the device channel 110 of the endoscope 100 and is configured as the suction channel 10. The proximal end of the sheath is configure as an adaptor 12 of the suction channel 10, being connected to the vacuum source or irrigation pump through pipe lines (there is a surgery debris collector which is not shown in the specifications because it is the standard industrial arts), the distal end of the sheath is open as suction window 11. The window 11 can be open in the distal end face of the sheath 10, or open in combined part of the terminus and part of the side of the sheath shown in FIG. 3B, or open completely in the side of the sheath shown in FIG. 3A, varies in different embodiments. The materials of the sheath should be biocompatibility such as stainless steel, polymer etc. The material can be transparent or opaque, can be rigid or flexible.

A conduit limits and provides the fiber path 20 of the optic fiber 30. The inner diameter of the conduit is a little large than the outer diameter of the fiber allowing the fiber 30 can pass through. The distal end 21 of the fiber conduit is the open allowing fiber 30 to protrude.

In order to make the window 11 and window 31 as close as possible and reduce the total size of the cross-section, the suction sheath 10 and fiber conduit 20 are integrated as a whole through welding, bonding and molding. The integrated result is that the center axis of sheath and the conduit are paralleled to each other.

Figure 3A:
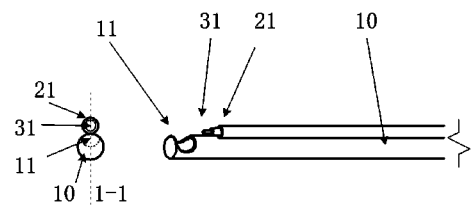
FIG. 3A is one embodiment of the invention depicting the suction window is in the side of the suction sheath of the distal end.

In FIG. 3A the window 11 is open completely in the side of sheath distal end and the maximum open size should be less or equal to the inner diameter of the sheath 10. The sheath 10 and the fiber conduit 20 is integrated in the manner that they contact with each other externally, the fiber laser window 31 can be extended across the center line 1-1 of window 11 viewing in the end, the end 21 of the fiber conduit 20 is about 5-10 mm away from the nearest border of window 11.

Figure 3B:
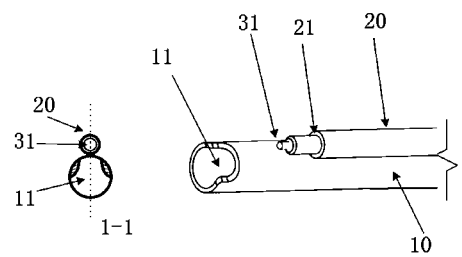
FIG. 3B is one embodiment of the invention illustrating the suction window is in both parts of the terminus and the side of the sheath of the distal end.

In FIG. 3B, the suction window 11 is patterned opening in both parts of the end terminal and side of the sheath 10, the maximum open size should be less or equal to the inner diameter of the sheath 10. The sheath 10 and the fiber conduit 20 is integrated in the manner that they contact with each other externally, the fiber laser window 31 can be extended across the center line 1-1 of window 11 viewing in the end, the end 21 of the fiber conduit 20 is about 5-10 mm away from the nearest border of window 11.

In the two embodiments shown in FIG. 3, the 5-10 mm distance is help to have good vision of the surgery through the endoscope camera 120.

As the result of the embodiments, the laser window 31 of the fiber 30, emitting laser, is approaching to the suction window 11 and the surgery targets which are being sucked to the window 11 when the suction is applied through suction channel.

Figure 5:
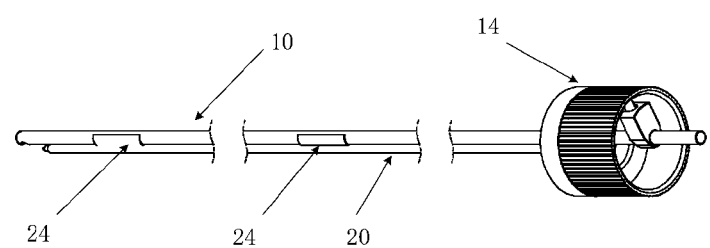
FIG. 5 One embodiment can change the relative position between the suction window and the fiber tip.
Figure 8:
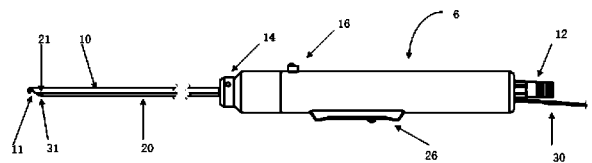
FIG. 8 is the exterior view of one embodiment of the invention.

The construction of the suction sheath 10 and fiber conduit 20 can be embodied as shown in FIG. 5 where the fiber conduit 20 can be turned around the axis of the suction sheath 10. The two parts 24 which is bond to fiber conduit 20 further limit the round movement around the suction sheath 10. The round movement either in CW or in antiCW of fiber conduit 20 is activated by turning the turning parts 14. That movement is limited to saying 30° depending on the size of window 11. That movement benefits the fiber laser window 31 approaching the surgery targets. As shown in FIG. 8, the turning part 14 is integrated as part of the probe handpiece 6 through threaded pattern.

This invention is susceptible of embodiment in many different forms. The configuration of the fiber conduit 20 and the suction sheath 10 is not limited the touching manner, which includes both the inner contacting and outside contacting manner. There is an embodiment that the fiber conduit 20 is in the axis of the suction sheath 10 and the window 11 is opened in the terminal of the suction sheath 10.

Figure 4:
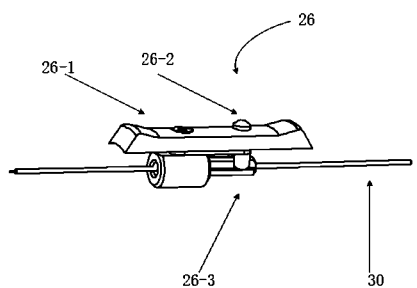
FIG. 4 depicts one embodiment of the fiber position regulator.

There are two operating modes related to fiber position regulator 26 shown in FIG. 4. One operating mode is the length the fiber tip moved within 10 mm, which is achieved through the bush button 26-1 of the fiber position regulator 26 through the thumb of the doctor. The fiber position regulator 26 can push the fiber forward and backward along the fiber conduit 20 no matter it is during surgery procedures or not. If length of the movement of fiber tip beyond 10 mm is desired, another operating mode is to push bottom 26-2 to release the fiber from griping by the part 26-3 of the regulator 26, fiber 30 can be moved forward or backward by directly handing the fiber 30 itself from the doctor. Through the fiber position regulator 26, 3 objectives are accomplished. First is to adjust the position of fiber laser window 31 coincident with the suction window 11 in order to achieve the good interaction between the laser and the surgery targets such calculus. The second is to adjust the fiber laser window 31 forward to its right position when the fiber tip is born back, or being destroyed during the procedures. The third is to move fiber forward enough to arrow the doctors to repair the fiber tip, after the fiber tip is repaired then move the fiber tip backward to the position of the suction window 11.

The principal of this invention is build a suction channel and window which can capture the surgery targets and the debris correctly without the hinder of fiber tips. While the good interaction between the infrared laser and the surgery targets is disclosed through the construction pattern of fiber conduit where position and limit the optic fiber tip approaching the surgery targets, being kept in position of the suction window during the procedures. The fiber tip position can be adjusted during the procedures through the fiber position regulator or the related turning movement of the fiber tube against the suction channel.

Figure 6:
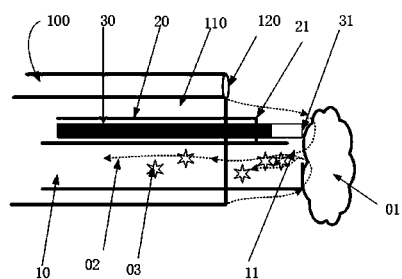
FIG. 6 is the cross-section view of the suction channel of the debris and irrigation water though the embodiment with suction window on both the terminus and side of the sheath.
Figure 7:
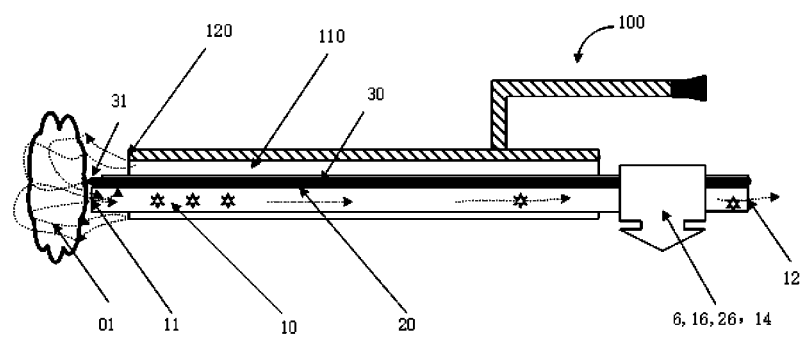
FIG. 7 illustrates the laser fiber probe within the endoscope to treat calculus during laser lithotripsy procedure.

When the arrangement of the suction channel 10 and fiber conduit 20 are in the outside of each other as shown the embodiments in FIG. 3, the total size of the whole should be less than the diameter of the device channel 110 of the endoscope 100 as shown in FIG. 7. This size requirement can guarantee the laser fiber probe can pass through the endoscope to reach the surgery targets. In FIG. 6, the fiber laser window 31 and suction window 11 should be protruded out of the endoscope 100 in the manner which the fiber laser window 31 is under the monitoring of the camera 120 of the endoscope.

There are different embodiments of the probe which can either has the suction switcher 16 or not. The switcher 16 can not just only turn on or off the suction channel 10, but also other important role is to keep very good interactions between the infrared laser pulse and the surgery targets. This is because that at first the debris is peeled out of the calculus where the fiber laser window 31 is pointed, as laser pulse keeps firing the interaction will become poor because the separation between the window 31 and calculus become larger. However the calculus position against the suction window will be repositioned once the suction is switched off and on again. In addition to on and off conditions of switcher 16, there are other embodiments to have partial on and off instead just on and off as options, which can help to maintain the proper suction forces. The switcher 16 is installed in the handpiece 6 of the fiber laser probe in the embodiment shown in FIG. 8.

In the embodiment of the invention shown in FIG. 8, handpiece 6 is part of the probe. The handpiece is also integrated with the suction switcher 16, fiber position regulator 26 and turning part 14. This kind of configuration facilitates the doctors to manipulate the probe in one hand during surgery procedures. Of course the probe is not necessary to have hand piece, the probe can be just the bonded suction sheath and fiber conduit which is either operated by doctors or part of robots.

In a particular laser surgery procedure of one embodiment shown in FIG. 8, the fiber 30 is installed into the fiber conduit 20 through release button 26-2 before the procedure. To adjust the fiber laser window 31 to the position of the suction window 11 through button 26-1 after the button 26-2 is closed. Before the probe is connected to vacuum source, close the switcher 16 and make the connection of the vacuum source. Now the probe is ready. Place the probe through the device channel 110 of endoscope 100 until the suction window 11 reaching the surgery targets such as calculus shown in FIG. 7. To activate switcher 16, the calculus is sucked to the window 11 and window 31 at the same time, then firing the infrared laser, the fragmented pieces of calculus are absorbed by the vacuum source away from the window 11 and pass all the way of the suction channel 10, suction connector 12 and the pipe lines, finally are collected. The fragmentation and evacuation of the calculus are coincidence in this laser surgery procedure with the invented probe. In case the fiber tip or fiber laser window is born back, or is broken, the laser induced fragmentation of the calculus becomes slow, the doctor can improve the result through the forward movement of the fiber laser window 31 with the usage of the regulator 26. In case the fragmentation of the calculus becomes slow, the good interaction between the laser energy and the surgery targets can be resumed just through turning on or off the suction channel through switcher 16. An alternative way is to turn the turning part 14 clock-wise or anti clock-wise to reposition the window 31 against calculus after turn-off the suction channel 10.

As shown in FIGS. 6 and 7, the irrigation water together with the surgery debris are forced into the suction channel 10 through the entrance where is the window 11. Herein the suction channel 10 is connected through adaptor 12 to a vacuum source or irrigation pump via the pipe lines, which becomes the external force of the suction window 11 of the fiber laser probe.

The invention claimed is:

1. A laser fiber probe comprising of, a suction sheath and a fiber conduit, which are combined together, and a suction switcher:
   suction sheath: an opening, either completely in the side, or in combination of part the terminal and the side, is in the distal end of the suction sheath and is used to suck the surgery targets and surgery debris, wherein the proximal end of the suction sheath is adapted to connect to at least a suction source or an irrigation pump;
   fiber conduit: a fiber position regulator functions to move forward or backward of the fiber tip to approach the suction opening;
   suction switcher: turn partially or completely on and off to adjust the position of surgery target relative to the suction opening.

2. The laser fiber probe of claim 1, wherein the position of the suction sheath and the fiber conduit is fixed.

3. A laser fiber probe comprising of two parts, a suction sheath and a fiber conduit, which are combined together, wherein the relative position of the suction sheath and the fiber conduit can be changed through circular movement:
   suction sheath: an opening, either completely in the side, or in combination of part the terminal and the side, is in the distal end of the suction sheath and is used to suck the surgery targets and surgery debris, wherein the proximal end of the suction sheath is adapted to connect to at least a suction source or an irrigation pump;
   fiber conduit: a fiber position regulator functions to move forward or backward of the fiber tip to approach the suction opening; can revolve around the suction sheath to keep fragmenting surgery target within 30-degree angle depending on size of the suction sheath opening.

4. The laser fiber probe as in either claim 1 or claim 3, wherein the suction sheath and the fiber conduit is made from rigid materials, or flexible materials.

5. The laser fiber probe of claim 3, further comprising a suction switcher.

6. The laser fiber probe as in either claim 1 or claim 3, wherein the suction sheath and the fiber conduit is made from transparent material, or opaque material.

7. The laser fiber probe as in either claim 1 or claim 3, wherein the fiber conduit is in touching with the outside or inside of the suction sheath, or just inside of the suction sheath.

* * * * *